(12) United States Patent
Ticehurst et al.

(10) Patent No.: US 10,370,402 B2
(45) Date of Patent: Aug. 6, 2019

(54) PROCESS FOR THE PREPARATION OF FLUTICASONE PROPIONATE FORM 1

(75) Inventors: Martyn David Ticehurst, Kent (GB); Ivan Marziano, Kent (GB); Eleftherios Kougoulos, Morrisville, NC (US)

(73) Assignee: Pfizer Limited, Sandwich, Kent (GB)

( * ) Notice: Subject to any disclaimer, the term of this patent is extended or adjusted under 35 U.S.C. 154(b) by 300 days.

(21) Appl. No.: 14/131,407

(22) PCT Filed: Jul. 6, 2012

(86) PCT No.: PCT/US2012/045660
§ 371 (c)(1),
(2), (4) Date: Jan. 7, 2014

(87) PCT Pub. No.: WO2013/009591
PCT Pub. Date: Jan. 17, 2013

(65) Prior Publication Data
US 2014/0141247 A1    May 22, 2014

Related U.S. Application Data

(60) Provisional application No. 61/505,612, filed on Jul. 8, 2011.

(51) Int. Cl.
C07C 22/00    (2006.01)
C07C 303/00    (2006.01)
(Continued)

(52) U.S. Cl.
CPC ............. *C07J 31/00* (2013.01); *C07J 31/006* (2013.01); *A61K 9/0075* (2013.01); *C07B 2200/13* (2013.01); *Y10T 428/2982* (2015.01)

(58) Field of Classification Search
CPC ............................. B01F 11/0258; A61K 9/14
(Continued)

(56) References Cited

U.S. PATENT DOCUMENTS 5,254,330 A * 10/1993 Ganderton ............. A61K 47/26
424/434
6,221,398 B1 * 4/2001 Jakupovic ............ A61K 9/0075
424/489
(Continued)

FOREIGN PATENT DOCUMENTS

GB        2088877      6/1982
WO        00/38811     7/2000
(Continued)

OTHER PUBLICATIONS fda.gov, Reference ID: 3705083 (2015)—(link: www.accessdata.fda.gov/ drugsatfda_docs/label/2015/202236s008lbl.pdf.*
(Continued)

*Primary Examiner* — Hoa (Holly) Le
(74) *Attorney, Agent, or Firm* — Sorell, Lenna & Schmidt LLP; William D. Schmidt

(57) ABSTRACT

The invention relates to a novel crystallization process for preparing fluticasone propionate as crystalline form 1 polymorph with controlled particle size and suitable for micronization. Said process comprises the step of dissolving fluticasone propionate in acetone or in a mixture of acetone and water and then adding this solution to water or to a mixture of water 10 and acetone, thereby causing fluticasone propionate to crystallize out of the solution as crystalline form.

19 Claims, 10 Drawing Sheets

Figure 1:
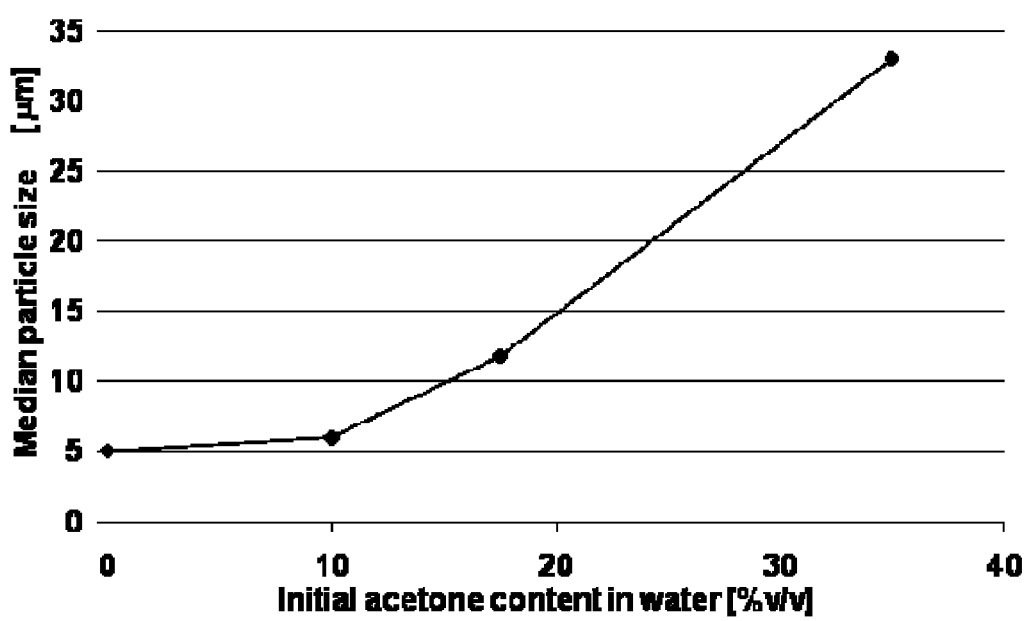

(51) Int. Cl.
    *C07C 321/00*     (2006.01)
    *C07J 31/00*     (2006.01)
    *A61K 9/00*     (2006.01)

(58) Field of Classification Search
    USPC ....... 562/426, 427, 432, 490, 492, 474, 840, 562/849, 866
    See application file for complete search history.

(56) References Cited

U.S. PATENT DOCUMENTS

| | | | |
|---|---|---|---|
| 6,406,718 B1* | 6/2002 | Cooper | 424/489 |
| 6,482,438 B1* | 11/2002 | Singh | A61K 9/1688 424/450 |
| 2003/0181432 A1* | 9/2003 | Lancaster et al. | 514/175 |
| 2004/0258756 A1* | 12/2004 | McLoughlin | A61K 9/14 424/489 |
| 2005/0222107 A1 | 10/2005 | Coote et al. | |
| 2006/0137598 A1* | 6/2006 | Kozyuk | C30B 7/00 117/11 |

FOREIGN PATENT DOCUMENTS

| | | |
|---|---|---|
| WO | 0038811 | 7/2000 |
| WO | 01/32125 A1 | 5/2001 |
| WO | 03/061816 | 7/2003 |
| WO | 03/066653 | 8/2003 |
| WO | 2004/001369 | 12/2003 |
| WO | 2005002654 | 1/2005 |

OTHER PUBLICATIONS

Tamura et al, Advances in Organic Crystal Chemistry: Comprehensive Reviews 2015, p. 153.*

Sander et al., Sonocrysallization and sonofragmentation, Ultrasonics Sonochemistry 21 (2014) 1908-1915.*

Stieger et al., Recrystallization of Active Pharmaceutical Ingredients, Crystallization—Science and Technology, Sep. 19, 2012—ISBN 978-953-51-0757-6.*

McBride and Carter, Spontaneous Resolution by Stirred Crystallization, Angew. Chem. Int. Ed. Engl. 30 (1991) No. 3 (Year: 1991).*

Kondepudi & Sabanayagam, Secondary nucleation that leads to chiral symmetry breaking in stirred crystallization, vol. 217, Issue 4, 1994, 364-368 (Year: 1994).*

Kondepudi et al, Kinetics of chiral symmetry breaking in crystalllization, J. Am. Chem. Soc. 1993, 115, 10211-10216 (Year: 1993).*

Agrawal, Investigation and Optimization of a solvent/anti-solvent crystallization process for the production of inhalation particles, VCU Theses and Dissertations, Jul. 2010.*

Agrawal, VCU Thesis and Dissertations—Investigation and optimization of a solvent/antisolvent crystallization process for the production of inhalation particles, 2010 (Year: 2010).*

Murnane, et al., "Crystallization and Crystallinity of Fluticasone Propionate", Cryst. Growth Des., 2008, 8 (8), pp. 2753-2764.

International Search Report for PCT/US2012/045660 dated Oct. 16, 2012.

"Extended European Search Report for EP12811395.8 dated Nov. 28, 2014".

Steckel, et al., "In vitro characterization of jet-milled and in-situ micronized fluticasone-17-propionate", International journal of Pharmaceutics, vol. 258, Jan. 1, 2003, pp. 63-75.

Gracin, et al., "Influence of Ultrasound on the Nucleation of Polymorphs of p-Aminobenzoic Acid", Crystal Growth & Design, vol. 5, No. 5, 2005, 1787-1794.

Price, et al., "Composition of Calcium Carbonate Polymorphs Precipitated Using Ultrasound", Crystal Growth & Design, vol. 11, No. 1, 2011, 39-44.

* cited by examiner

PROCESS FOR THE PREPARATION OF FLUTICASONE PROPIONATE FORM 1

The present invention relates to a novel crystallisation process for preparing fluticasone propionate as crystalline form 1 polymorph with controlled particle size and suitable for micronisation.

Fluticasone propionate is a corticosteroid acting as a potent anti-inflammatory and which is used as crystalline form 1 in the treatment of rhinitis, eczema, psoriasis, asthma and COPD. It has the chemical name S-(fluoromethyl)-6α, 9-difluoro-11β-17-dihydroxy-16α-methyl-3-oxoandrosta-1,4-diene-17β-carbothioate, 17-propionate and the following chemical structure:

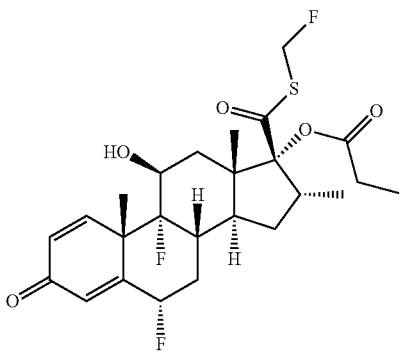

Several processes for preparing fluticasone propionate, in particular as its stable crystalline form 1, have been described in the literature. For example, WO 00/38811 discloses the crystallisation of fluticasone propionate dissolved in acetone by mixing with water in the presence of ultrasound radiation. WO 01/32125 discloses the crystallisation of fluticasone propionate by admitting a stream of solution of fluticasone propionate in acetone and a stream of water as anti-solvent tangentially into a cylindrical mixing chamber having an axial outlet port such that said streams are intimately mixed through formation of a vortex. However, these processes are not easily scalable and use complex apparatus and technologies (such as use of ultrasound).

Other, more simple, crystallisation processes have also been proposed. For example, the so-called crystalline form 1 of fluticasone propionate can be obtained by dissolving the crude product as obtained in e.g. GB 2088877 in ethyl acetate and then re-crystallising. Alternatively, a method for preparing fluticasone propionate as crystalline polymorphic form 1 by mixing a solution of fluticasone propionate in a non-solvating organic liquid solvent such as methyl acetate, ethyl acetate or pentanone, with a non-solvating organic liquid anti-solvent such as toluene, isooctane or hexane thereby causing fluticasone propionate as crystalline form 1 to crystallise out of the solution has been described in WO 03/066653. However, it has been found that these crystallisation processes do not offer control and flexibility in terms of output particle size distribution for fluticasone propionate. Similar to the majority of drugs intended for delivery to the lung, fluticasone propionate is usually subjected to micronisation prior to formulation to enable production of appropriately sized respirable particles. It is however well known from the literature that there is a link between the particle size of ingoing material and the size of micronized product, hence it is of key importance to precisely control the particle size of the material that is fed into the microniser to ensure reliable and effective drug delivery to the lung.

The present invention represents a solution to the above mentioned problems. The present invention is indeed directed to a new crystallisation process for preparing fluticasone propionate as crystalline form 1 which is scalable, reproducible and does not involve complex apparatus. The crystallisation process according to the present invention also enables more flexibility and precise control of product particle size distribution through variations in solvent composition. Finally the crystallisation process according to the present invention shows lower product loss in the micronisation chamber compared to a traditional anti-solvent crystallisation.

The present invention is thus directed to a process for preparing fluticasone propionate as crystalline form 1, which comprises the step of dissolving fluticasone propionate in acetone or in a mixture of acetone and water and then adding this solution to water or to a mixture of water and acetone, thereby causing fluticasone propionate to crystallise out of the solution as crystalline form 1.

According to the present invention, the water or water/acetone mixture in which the fluticasone propionate solution is added may also be referred as the "non-solvent" or the "non-solvating mixture" respectively.

According to an embodiment, fluticasone propionate is dissolved in acetone containing 0 to 10% water, and the resulting solution is added to water containing 0 to 35% acetone. Preferably, fluticasone propionate is dissolved in acetone, and the resulting solution is added to water containing 0 to 30% acetone.

According to another embodiment, a solution is prepared through dissolving fluticasone propionate in acetone or an acetone/water mixture with concentrations between 30 and 50 grams per liter of solvent. Preferably, said solution is prepared through dissolving fluticasone propionate in acetone or an acetone/water mixture with concentrations between 35 and 45 grams per liter of solvent.

According to a further embodiment, fluticasone propionate is dissolved in 1 volume of acetone or acetone/water mixture and this solution is then added to a volume of water or water/acetone mixture comprised between 0.65 and 1.35. Preferably, 1 volume of the fluticasone propionate solution is added to a volume of water or water/acetone mixture comprised between 0.8 and 1.2. More preferably, 1 volume of the acetone/fluticasone propionate solution is added to a volume of water or water/acetone mixture of about 1.

According to another embodiment, the addition takes place at a temperature comprised between 10° C. and 40° C. Preferably, the addition takes place at ambient temperature.

According to another embodiment, the addition takes place over a period comprised between 10 minutes and 6 hours. Preferably, the addition takes place over a period comprised between 30 minutes and 2 hours. More preferably, the addition takes place over a period of about 1 hour.

According to another embodiment, the addition of the fluticasone propionate solution occurs via a pump in the form of pulsed aliquots.

During and following from the addition of the fluticasone propionate solution into the non-solvent or non-solvating mixture, nucleation and growth of fluticasone propionate occur. Once the fluticasone propionate solution addition into the non-solvent or non-solvating mixture is completed, the slurry formed is stirred over a period comprised between 0 and 12 hours, followed by filtration and drying. Preferably, the slurry is stirred over a period of comprised between 1 hour and 10 hours. More preferably, the slurry is stirred over a period comprised between 4 hours and 8 hours. Still more preferably, the slurry is stirred over a period of about 1 hour.

Figure 2:
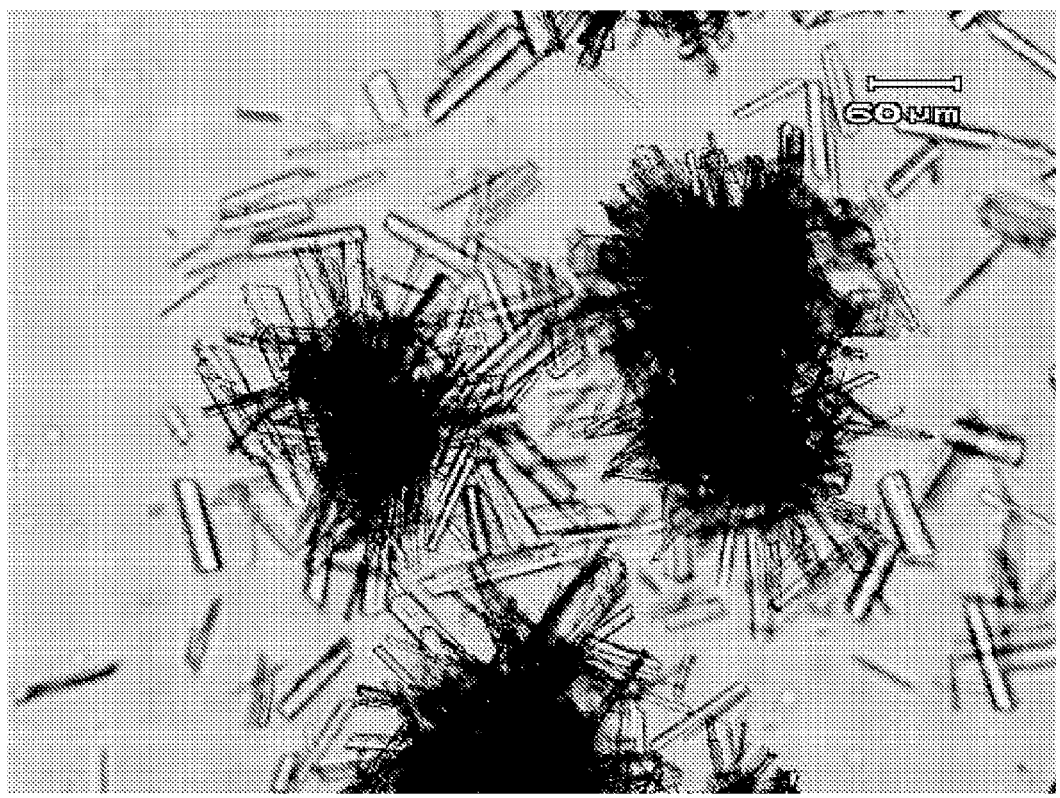

The process according to the present invention is particularly advantageous since it allows good flexibility and control of the physical properties of the fluticasone propionate obtained, in particular the size and shape of the particles obtained. This is exemplified in FIG. 1, showing the dependence of particle size on solvent composition when fluticasone propionate is crystallised using the process described in the present invention. Surprisingly, it has been found that the specific reverse anti-solvent crystallization process according to the present invention allows the crystallization of fluticasone propionate with different particle sizes through variations in solvent composition and also delivers fluticasone propionate particles which do not exhibit the agglomeration which is typical of conventional anti-solvent crystallization, as described for example by Murnane et al. in Cryst. Growth Des. 2008, 8, 2753-2764 and as illustrated in FIG. 2.

In addition to influencing the efficacious delivery of intra-nasal and pulmonary drug formulations, control of physical properties of fluticasone propionate is also important since these properties influence bulk density, flow and downstream processing characteristics of the product.

Typically, the process according to the present invention yields particles that are 5-200 µm in length with a width of 3-30 µm. The fluticasone propionate particles obtained by the process according to the present invention thus have the most appropriate design, in particular for micronisation and formulation with lactose as a dry powder and administration with a dry powder inhaler such as the device described in e.g. WO 2005/002654. The particles of fluticasone propionate obtainable from the herein described crystallisation process thus constitute another object of the present invention.

An additional and significant advantage of the particles resulting from the process according to the present invention is the increased yield in micronized fluticasone propionate due to lower loss of product in the jet milling chamber, compared to micronisation input obtained from a conventional anti-solvent process Fluticasone propionate may be prepared according to any of the processes known from the literature such as e.g the process described in GB 2088877. Alternatively, fluticasone propionate is also commercially available for a number of suppliers, e.g. Hovione, Sterling or NewChem.

The particles of fluticasone propionate as obtained from the crystallisation process according to the present invention may be micronized to a controlled size and formulated with lactose so as to form a dry powder blend.

Fluticasone propionate as obtained from the process according to the present invention is particularly suitable for micronisation and administration by inhalation from a dry powder inhaler. Typically, it is administered in the form of a dry powder as a mixture with lactose.

To that effect, the particles of fluticasone propionate as obtained from the process according to the present invention are micronized by jet milling, and subsequently blended with lactose. The lactose used according to the present invention may be anhydrous or in the form of the monohydrate. Preferably, α-lactose monohydrate is used. The blend thus obtained is then suitable for filling into a dry powder inhaler.

The dosage unit is determined by a pre-filled capsule, blister or pocket or by a system that uses a gravimetrically fed dosing chamber. Units in accordance with the invention are typically arranged to administer a metered dose or "puff" containing from 50 to 500 µg of fluticasone propionate as obtained from the process according to the present invention. The overall daily dose will typically be in the range of 50 µg to 2 mg which may be administered in a single dose or, more usually, as divided doses throughout the day.

The fluticasone propionate obtained from the process according to the present invention may be administered alone or in combination with one or more other drugs. Suitable examples of other therapeutic agents which may be used in combination with fluticasone propionate include, but are by no means limited to $f_2$ agonists, preferably long-acting $\beta_2$ agonists, and M3 muscarinic antagonists, preferably long-acting M3 muscarinic antagonists.

Examples of suitable $\beta_2$ agonists include in particular salbutamol, terbutaline, bambuterol, fenoterol, salmeterol, formoterol, tulobuterol and their salts. Preferably the $\beta_2$ agonist is selected from salmeterol or formoterol and their salts. More preferably, the $\beta_2$ agonist is salmeterol xinafoate.

Examples of suitable M3 muscarinic antagonists include in particular ipratropium, oxitropium, tiotropium and their salts. Preferably the M3 muscarinic antagonist is tiotropium bromide.

According to a preferred embodiment, fluticasone propionate as obtained from the process according to the present invention is administered by inhalation as a dry powder either alone or in combination with salmeterol xinafoate.

The figures and examples below further illustrate the present invention.

FIGURES

FIG. 1 of 10: Effect of acetone % in the anti-solvent mixture on the volume median diameter D[v, 0.5] for a reverse anti-solvent process.

FIG. 2 of 10: Crystals of fluticasone propionate obtained from example 1.

Figure 3:
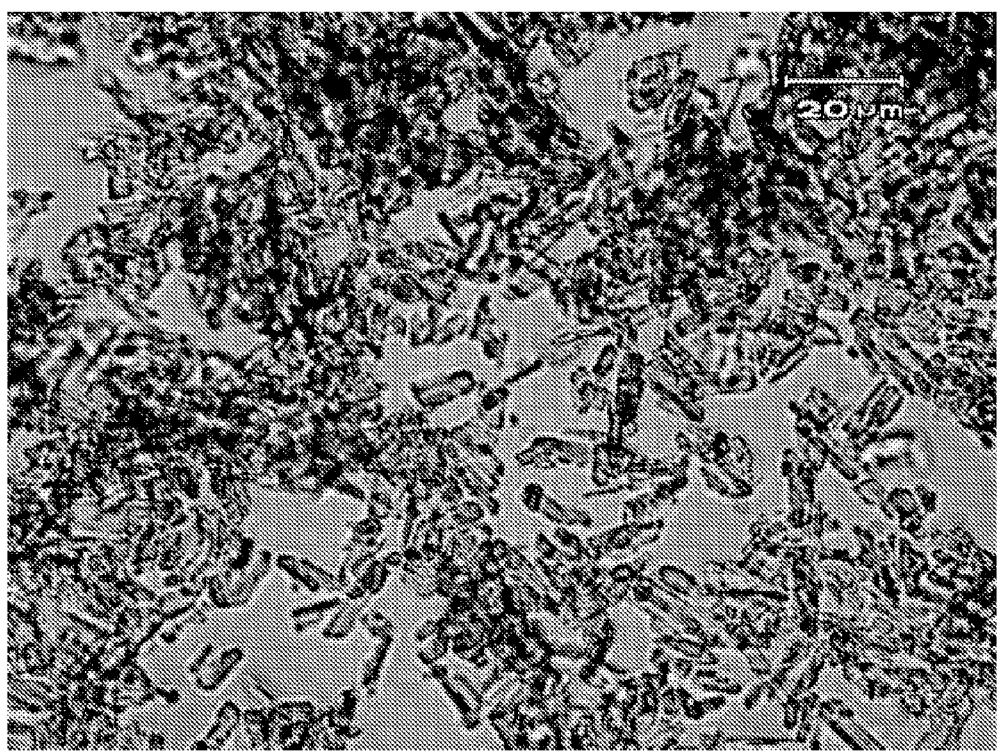

FIG. 3 of 10: Crystals of fluticasone propionate obtained from example 2.

Figure 4:
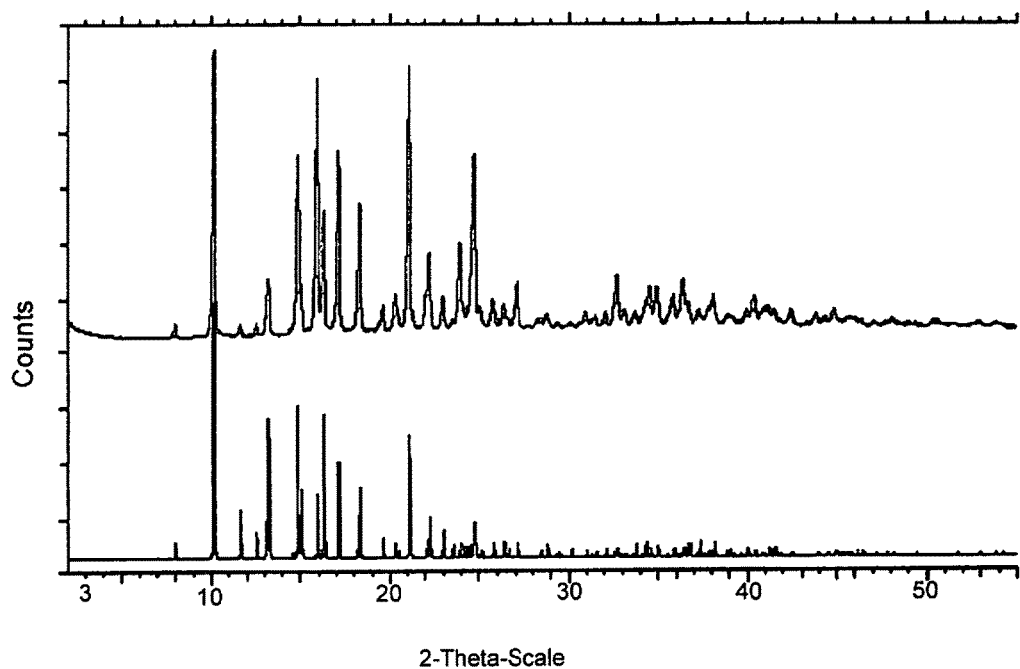

FIG. 4 of 10: PXRD patterns for Example 2 product (top line) and reference fluticasone propionate form 1 pattern for comparison (bottom line).

Figure 5:
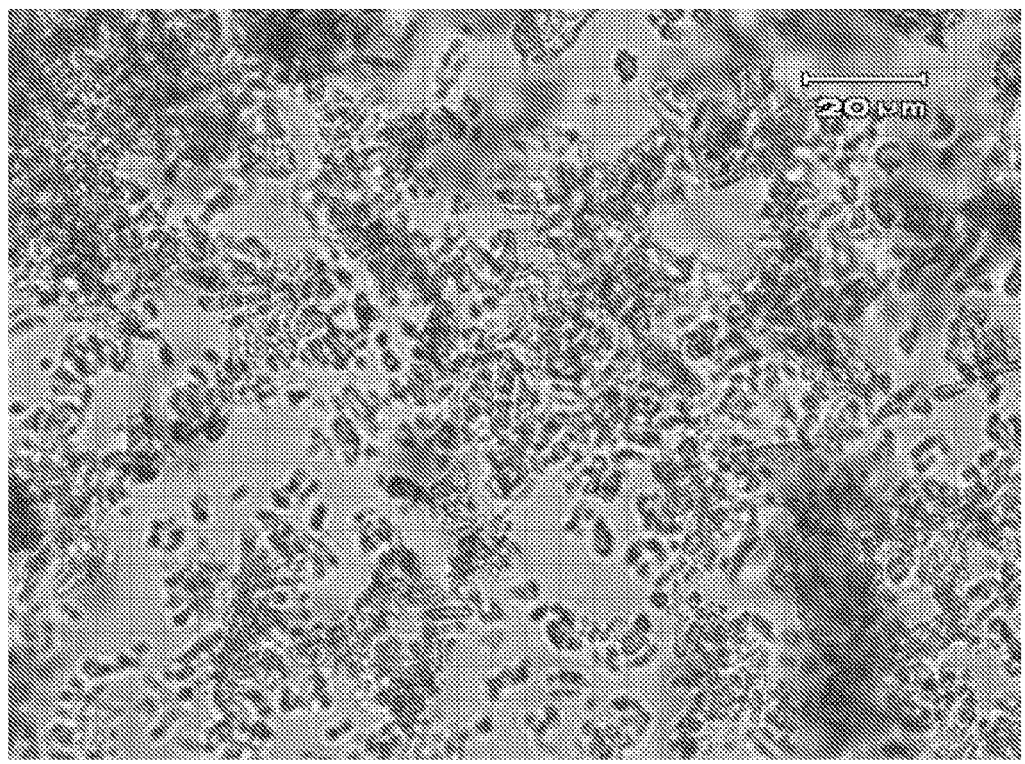

FIG. 5 of 10: Crystals of fluticasone propionate obtained from example 3.

Figure 6:
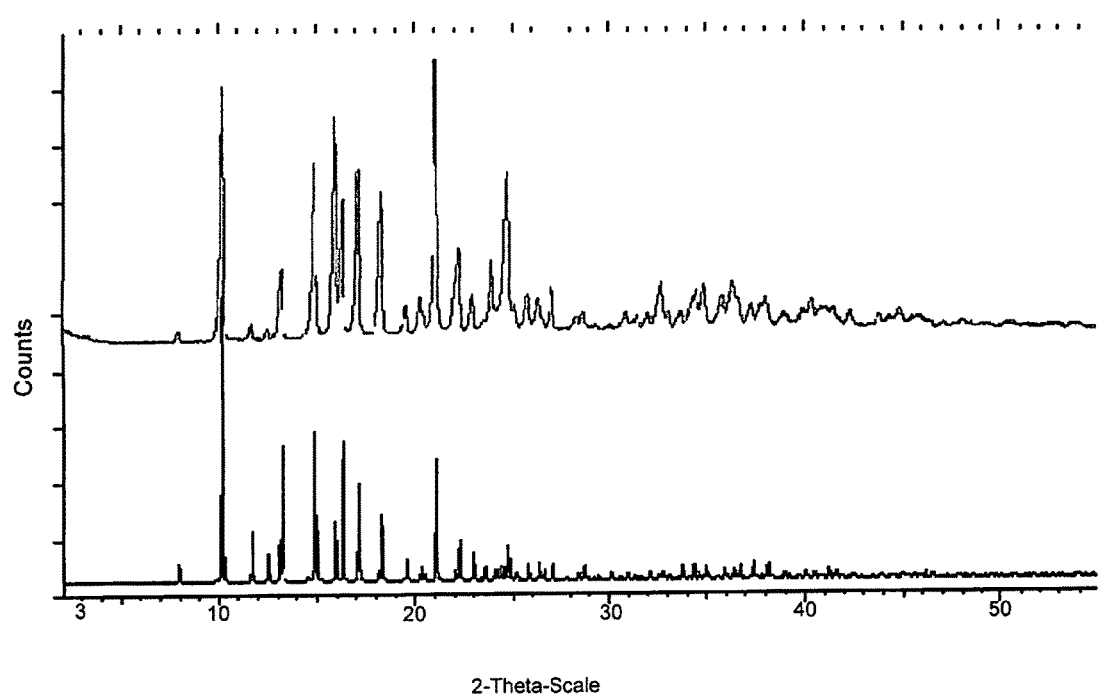

FIG. 6 of 10: PXRD pattern for example 3 product (top line) and reference fluticasone propionate form 1 pattern for comparison (bottom line).

Figure 7:
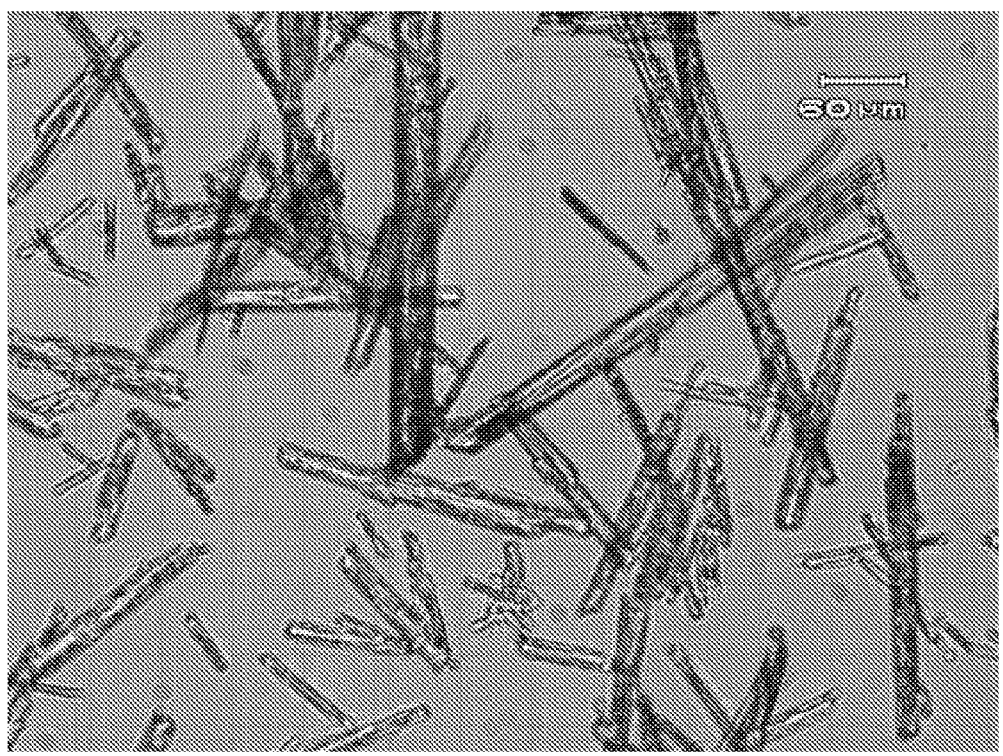

FIG. 7 of 10: Crystals of fluticasone propionate obtained from example 4.

Figure 8:
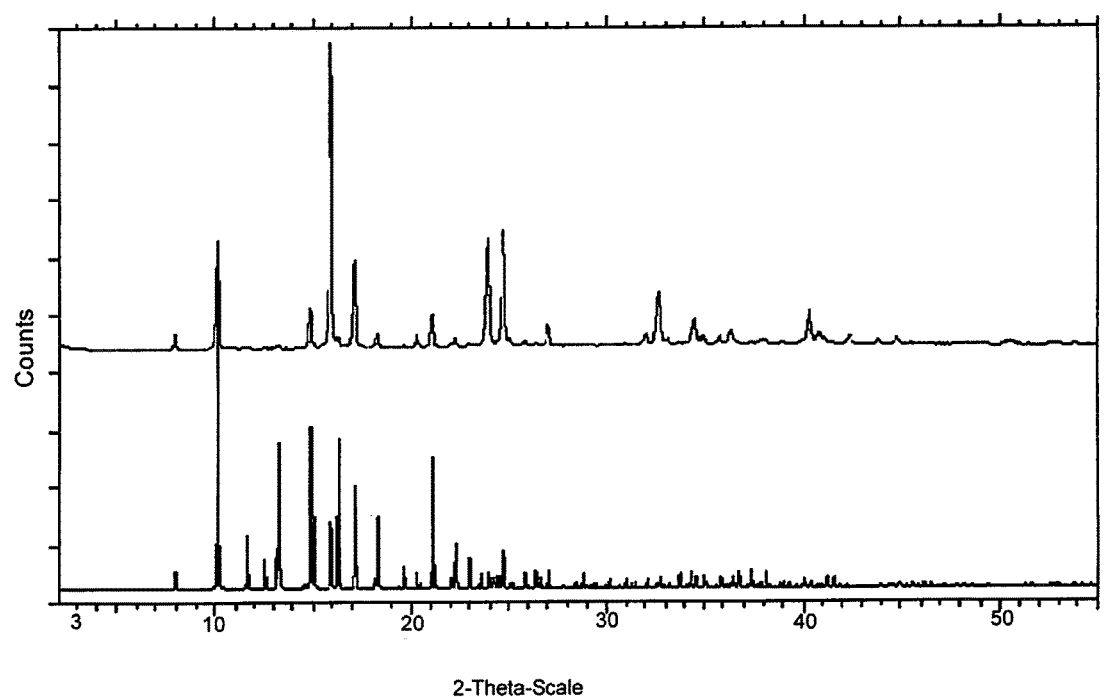

FIG. 8 of 10: PXRD pattern for example 4 product (top line) and reference fluticasone propionate form 1 pattern for comparison (bottom line).

Figure 9:
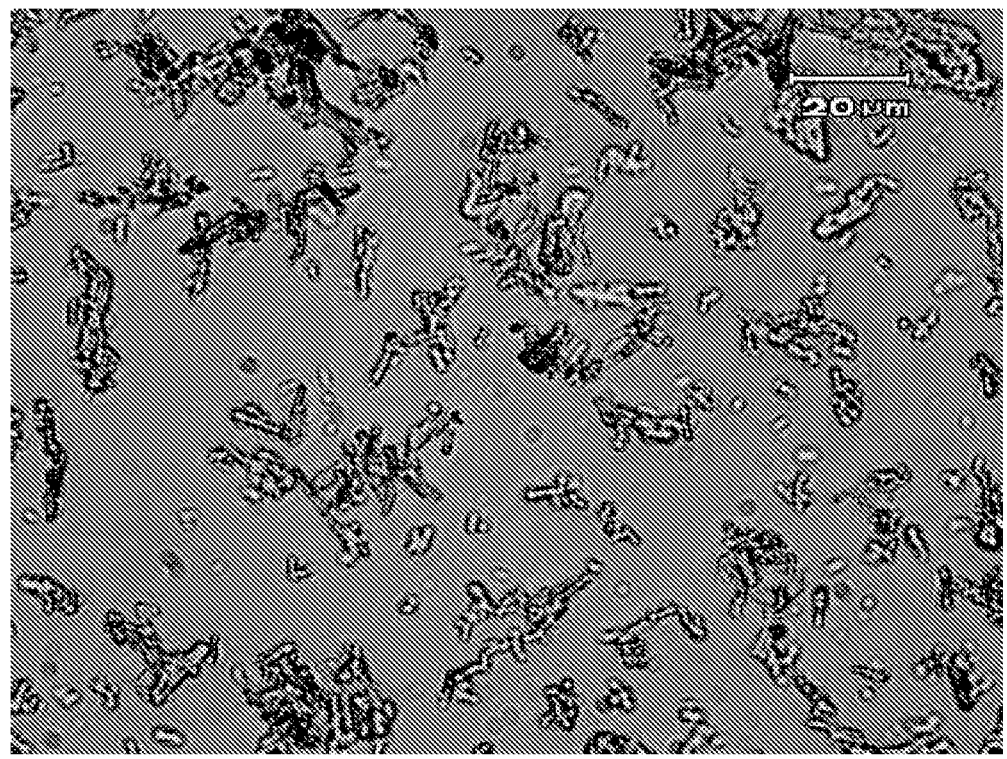

FIG. 9 of 10: Crystals of fluticasone propionate obtained from example 5.

Figure 10:
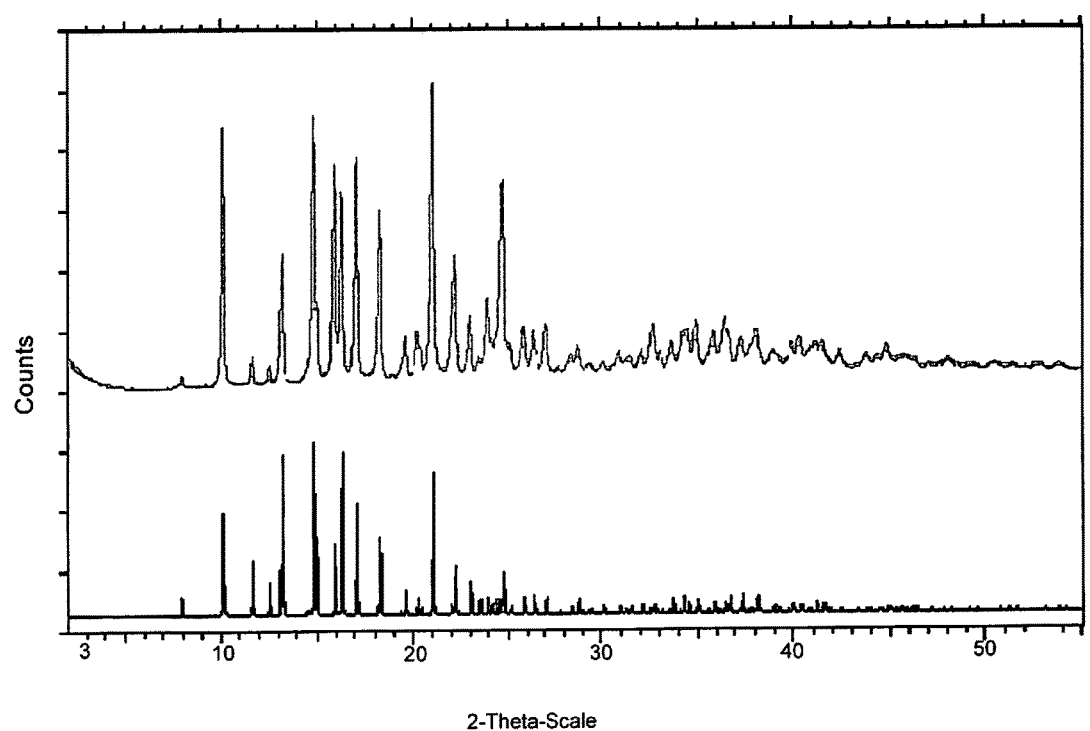

FIG. 10 of 10: PXRD pattern for example 5 product (top line) and reference fluticasone propionate form 1 pattern for comparison (bottom line).

EXAMPLES

Example 1: Re-Crystallisation of Fluticasone Propionate Using a Standard Anti-Solvent Process 1.0 g of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 25 mL acetone. The mixture was heated to 40° C., and then cooled to 20° C. 25 mL water was added to the solution at approximately 20° C. Crystallisation of the product was observed during the addition. The slurry was filtered under vacuum, and the isolated solid was dried in an oven at 50° C. under 0.9 bar vacuum, yielding fluticasone propionate Form 1. Crystals obtained from this experiment are shown in FIG. 2.

Example 2: Re-Crystallisation of Fluticasone Propionate Using the Reverse Anti-Solvent Process of the Present Invention 7.5 g of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 225 mL acetone. The mixture was heated to 40° C., and then cooled to 10° C. The chilled solution was added to a separate agitated vessel containing 225 mL water at 40° C. over a period of 10 minutes. Crystallisation of the product was observed during the addition. The mixture was cooled down to 20° C. and held at that temperature for 12 hours. The slurry was filtered under vacuum, and the isolated solid was dried in an oven at 50° C. under 0.9 bar vacuum, yielding 6.94 g of fluticasone propionate 30 (92.4% theoretical yield).

Crystals obtained from this experiment are shown in FIG. 3.

Powder X-Ray Diffraction Data

The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The peaks obtained were aligned against a silicon reference standard. The specimen was rotated whilst being irradiated with copper K-alpha1 X-rays (wavelength=1.5406 Ångstroms) with the X-ray tube operated at 40 kV/35 mA. The analyses were performed with the goniometer running in continuous mode set for a 0.2 second count per 0.018° step over a two theta range of 2° to 55°. Characteristic diffraction angles for the two known polymorphs of fluticaseon propionate, as reported in EU Patent EP 0 937 100 B1, are as indicated below in table 1:

TABLE 1

| Polymorph | Primary Peaks (°) | | Secondary peaks (°) | | | | | |
|---|---|---|---|---|---|---|---|---|
| Form 1 | 7.9 | 10.0 | 11.5 | 12.4 | 13.1 | — | 14.9 | — | 15.8 |
| Form 2 | 7.6 | 9.8 | — | — | 13.0 | 13.6 | — | 15.2 | — |

A PXRD pattern of the product obtained from this experiment, shown to match that of form 1 for fluticasone propionate, is shown in FIG. 4.

Example 3: Re-Crystallisation of Fluticasone Propionate Using the Reverse Anti-Solvent Process of the Present Invention 10 g of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 200 mL acetone. The mixture was heated to 40° C., and then cooled to 10° C. The chilled solution was added to a separate agitated vessel containing 200 mL water at 10° C. over a period of 10 minutes. Crystallisation of the product was observed during the addition. The mixture was heated to 20° C. and held at that temperature for 12 hours. The slurry was filtered under vacuum, and the isolated solid was dried in an oven at 50° C. under 0.9 bar vacuum, yielding 9.33 g of fluticasone propionate (93.3% theoretical yield).

Crystals obtained from this experiment are shown in FIG. 5.

A PXRD pattern from the product, shown to match that of form 1 for fluticasone propionate, is shown in FIG. 6.

Example 4: Re-Crystallisation of Fluticasone Propionate Using the Reverse Anti-Solvent Process of the Present Invention 9 g of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 270 mL acetone. The mixture was heated to 40° C., and then cooled to 10° C. The chilled solution was added to a separate agitated vessel containing 175 mL water and 75 mL acetone at 10° C. over a period of 6 hours. Crystallisation of the product was observed during the addition. The mixture was heated to 20° C. and held at that temperature for 12 hours. The slurry was filtered under vacuum, and the isolated solid was dried in an oven at 50° C. under 0.9 bar vacuum, yielding 8.56 g of fluticasone propionate (95.1% theoretical yield).

Crystals obtained from this experiment are shown in FIG. 7.

A PXRD pattern from the product, shown to match that of form 1 for fluticasone propionate, is shown in FIG. 8.

Example 5: Re-Crystallisation of Fluticasone Propionate Using the Reverse Anti-Solvent Process of the Present Invention 9 g of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 162 mL acetone and 18 mL water. The mixture was heated to 40° C., and then cooled to 10° C. The chilled solution was added to a separate agitated vessel containing 270 mL water at 10° C. over a period of 6 hours. Crystallisation of the product was observed during the addition. The mixture was heated to 20° C. and filtered under vacuum. The isolated solid was dried in an oven at 50° C. under 0.9 bar vacuum, yielding 7.56 of fluticasone propionate (84.0% theoretical yield).

Crystals obtained from this experiment are shown in FIG. 9.

A PXRD pattern from the product, shown to match that of form 1 for fluticasone propionate, is shown in FIG. 10.

Example 6: Re-Crystallisation of Fluticasone Propionate Using the Reverse Anti-Solvent Process of the Present Invention 0.958 Kg of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 24.7 L acetone. The mixture was heated to 35° C., and then cooled to 20° C. The solution was added to a separate agitated vessel containing 24 L water at 20° C. over a period of 2 hours. Crystallisation of the product was observed during the addition. The mixture was held at 20° C. for 1 hour with agitation. The slurry was filtered under vacuum, and the isolated solid was dried in an oven at 75° C. under 0.9 bar vacuum, yielding 0.85 Kg of fluticasone propionate (88.3% theoretical yield).

Example 7: Re-Crystallisation of Fluticasone Propionate Using the Reverse Antisolvent Process of the Present Invention 2.50 Kg of fluticasone propionate [S-(fluoromethyl)-6α, 9-difluoro-11β-17-dihydroxy-16α-25 methyl-3-oxoandrosta-1,4-diene-17β-carbothioate, 17-propionate] obtained from a commercial source was mixed with 62.5 L acetone. The mixture was heated to 35° C., and then cooled to 20° C. The solution was added to a separate agitated vessel containing 47 L water and 15.5 L acetone at 20° C. over a period of 2 hours.

Crystallisation of the product was observed during the addition. The mixture was held at 20° C. for 1 hour with agitation. The slurry was filtered under vacuum, and the isolated solid was dried in an oven at 75° C. under 0.9 bar vacuum, yielding 2.26 Kg of fluticasone propionate (90.4% theoretical yield).

Example 8: Re-Crystallisation of Fluticasone Propionate Using the Reverse Anti-Solvent Process of the Present Invention 9.5 Kg of fluticasone propionate [S-(fluoromethyl)-6α,9-difluoro-11β-17-dihydroxy-16α-methyl-3-oxoandrosta-1,4-diene-17β-carbothioate, 17-propionate] obtained from a commercial source was mixed with 237.5 L acetone. The mixture was heated to 35° C., and then cooled to 20° C. The solution was added to a separate agitated vessel containing 237.5 L water at 20° C. over a period of 4 hours. Crystallisation of the product was observed during the addition. The mixture was held at 20° C. for 4 hours with agitation. The slurry was filtered under vacuum, and the isolated solid was dried in an agitated dryer at 75° C. under 0.9 bar vacuum, yielding 8.5 Kg of fluticasone propionate (89.2% theoretical yield).

Example 9: Re-Crystallisation of Fluticasone Propionate Using the Reverse Anti-Solvent Process of the Present Invention 2.50 Kg of fluticasone propionate [S-(fluoromethyl)-6α, 9-difluoro-11β-17-dihydroxy-16α-methyl-3-oxoandrosta-1, 4-diene-17β-carbothioate, 17-propionate] obtained from a commercial source was mixed with 56.25 L acetone and 6.25 L water. The mixture was heated to 35° C., and then cooled to 20° C. The solution was added to a separate agitated vessel containing 40.6 L water and 21.9 L acetone at 20° C. over a period of 1 hour.

Crystallisation of the product was observed during the addition. The mixture was held at 20° C. for 1 hour with agitation. The slurry was filtered under vacuum, and the isolated solid was dried in an oven at 75° C. under 0.9 bar vacuum, yielding 2.15 Kg of fluticasone propionate (86.0% theoretical yield).

Example 10: Particle Size Data as Measured by Laser Diffraction

The following particle size assays for crystallised and micronized fluticasone propionate were used in this experiment:

Particle Size Method for Recrystallised FP:

The particle size distribution was measured on the Malvern Mastersizer 2000 laser diffraction system equipped with a Hydro 2000S liquid dispersion unit and flow cell. The sample was prepared by adding 15 drops of Tween 80 to crystallised fluticasone propionate within the glass 4 dram vial and mixing into a paste using a spatula, until all of the powder is wetted out and a smooth, uniform paste is achieved. Then the paste is added to the Hydro 2000S containing dispersant (0.1% Tween 80 in deionised water) using a spatula. When the obscuration target is achieved (20%±5%) the sample is left to stir within the Hydro 2000S for 1 minute to allow the particles to wet out, disperse and ensure a stable obscuration is achieved. Measurement is initiated after 1 minute of stirring.

Particle Size Method for Micronised FP:

The particle size distribution was measured on the Sympatec HELOS laser diffraction system (with R1 optical module giving a measuring range of 0.1/0.18-35 μm) together with SUCELL dispersing module. 100 mg of micronised sample is weighed into a 4-dram vial and 15 drops (approximately 0.5 mL) of Tween 80 is added from a 3 ml wide-tipped pipette to the powder. The mixture is then carefully stirred into a paste until all the particles are wetted out and a uniform smooth mixture is achieved. Then the paste is added to the SUCELL containing dispersant (0.025% Tween 80 in deionised water) using a spatula. Once the optical concentration target is achieved (10-15%) then a measurement is taken.

The particle size data expressed as D[v, 0.1], D[v, 0.5] and D[v, 0.9] obtained from examples 2-9 are summarized below in Table 2. D[v, 0.1], D[v, 0.5] and D[v, 0.9] represent the $10^{th}$ percentile volume diameter; $50^{th}$ percentile volume diameter; and $90^{th}$ percentile volume diameter respectively. In general the $n^{th}$ percentile volume diameter is defined so that n % of the particles have a volume equivalent particle diameter smaller than or equal to the $n^{th}$ percentile diameter. In the case of D[v, 0.5], it coincides with the median value.

TABLE 2

| Batch | D[v, 0.1] (μm) | D[v, 0.5] (μm) | D[v, 0.9] (μm) |
| --- | --- | --- | --- |
| Example 2 | 2.5 | 6.7 | 15.7 |
| Example 3 | 2.1 | 5.1 | 11.357 |
| Example 4 | 15.4 | 55.1 | 135.9 |
| Example 5 | 2.1 | 5.9 | 15.2 |
| Example 6 | 2.0 | 5.3 | 12.4 |
| Example 7 | 3.4 | 11.4 | 32.1 |
| Example 8 | 1.3 | 2.8 | 5.6 |
| Example 9 | 6.2 | 22.5 | 53.4 |

This experiment shows that the particle size distribution varies through variations in solvent composition.

Example 11: Particle Size Data Before and after Micronisation

Particles were micronized using a JetPharma MC150 (6 inch spiral jet mill) using the following conditions:
Feed rate: 15 g/min
Mill pressure: 3.5 bar
Venturi Pressure: 5.5 bar
Micronisation scale: 0.5 Kg.

The micronisation comparison of Examples 8 and 9 showing the impact of ingoing particle size on micronisation output is summarized in Table 3 below:

TABLE 3

| Batch | Ingoing particle size D[v, 0.5] (μm) | Post-micronisation particle size D[v, 0.5] (μm) |
|---|---|---|
| Example 8 | 2.8 | 2.3 |
| Example 9 | 22.5 | 4.0 |

Example 12: Product Recovery after Micronisation

An additional and significant advantage of the particles resulting from the process according to the present invention is the increased yield in micronized fluticasone propionate due to lower loss of product in the jet milling chamber, compared to micronisation input obtained from a conventional anti-solvent process such as the one described in Example 1. Several batches crystallised by either conventional anti-solvent techniques (as described in Example 1) or reverse anti-solvent techniques according to the present invention (as described Examples 2-9) were micronized, and the results summarised on Table 4 below show that the percentage of product collected after micronisation was on average much higher for reverse anti-solvent product batches than for conventional anti-solvent ones. Additionally, a much lower portion of product was left in the mill chamber if the product had originated from reverse anti-solvent.

TABLE 4

Summary of product recovery after micronisation for anti-solvent and reverse anti-solvent batches.

| Crystallization technique | % batch left in mill chamber | % batch recovered |
|---|---|---|
| Conventional anti-solvent technique | 10.6 | 53 |
| Conventional anti-solvent technique | 13.9 | 46.5 |
| Conventional anti-solvent technique | 5.5 | 35.6 |
| Conventional anti-solvent technique | 8.5 | 59.2 |
| Reverse anti-solvent according to present invention | 2.1 | 63.1 |
| Reverse anti-solvent according to present invention | 2.2 | 78.9 |
| Reverse anti-solvent according to present invention | 3.7 | 43.7 |
| Reverse anti-solvent according to present invention | 1.0 | 63.1 |
| Reverse anti-solvent according to present invention | 1.0 | 81 |

What is claimed is:

1. A process for preparing fluticasone propionate as crystalline polymorphic Form 1 having a controlled particle size, comprising: dissolving fluticasone propionate in a first volume of a solvent to form a solution; then adding the entire solution to a vessel containing a second volume of a non-solvent, forming a solvent/non-solvent slurry, thereby causing fluticasone propionate to crystallise out of the solution as crystalline Form 1; and, after said adding the entire solution is completed, holding the slurry, with agitation, in said vessel; wherein the solvent comprises acetone and from 0% to 10% water, based on the volume of the solvent; wherein the non-solvent comprises water and from 0% to 25% acetone, based on the volume of the non-solvent; and wherein the process is a batch process, and the controlled particle size has a 10th percentile volume diameter D[v, 0.1] of between 1.3 microns and 3.4 microns; a 50th percentile volume diameter D[v, 0.5] of between 2.8 microns and 11.4 microns; and a 90th percentile volume diameter D [v, 0.9] of between 5.6 microns and 32.1 microns.

2. A process according to claim 1, wherein fluticasone propionate is dissolved in the solvent in an amount between 30 and 50 grams per liter of solvent.

3. A process according to claim 1, wherein said adding the entire solution takes place at a temperature between about 10° C. and about 40° C.

4. A process according to claim 3, wherein said holding the slurry comprises stirring the slurry for a period of time, said period being between about 1 and about 12 hours, and wherein said holding is followed by filtration of the slurry to recover fluticasone propionate as crystalline Form 1 and drying of the recovered fluticasone propionate.

5. A process according to claim 1, wherein said adding the entire solution takes place over a period of between about 10 minutes and about 6 hours.

6. A process according to claim 1, wherein said adding the entire solution occurs via a pump in the form of pulsed aliquots.

7. A process according to claim 6, wherein said holding the slurry comprises stirring the slurry for a period of time, said period being between about 1 and about 12 hours, and wherein said holding is followed by filtration of the slurry to recover fluticasone propionate as crystalline Form 1 and drying of the recovered fluticasone propionate.

8. A process according to claim 1, wherein said adding the entire solution occurs over a period of between about 10 minutes and about 6 hours via a pump in the form of pulsed aliquots.

9. The process according to claim 1, wherein holding the slurry comprises stirring the slurry for a period of between about 1 and about 12 hours.

10. A process according to claim 1, wherein said holding the slurry comprises stirring the slurry for a period of time, said period being between about 1 and about 12 hours, and wherein said holding is followed by filtration of the slurry to recover fluticasone propionate as crystalline Form 1 and drying of the recovered fluticasone propionate.

11. The process according to claim 1, wherein a ratio of the first volume of the solvent to the second volume of the non-solvent is between 1:0.65 and 1:1.35.

12. The process according to claim 1, wherein: the non-solvent is water, and a ratio of the first volume of the solvent to the second volume of the non-solvent is 1:1.

13. The process according to claim 1, wherein: the non-solvent is a mixture of water and about 25% acetone, and a ratio of the first volume of the solvent to the second volume of the non-solvent is 1:1.

14. A process for preparing fluticasone propionate as crystalline polymorphic Form 1 having a controlled particle size, comprising: dissolving fluticasone propionate in a first volume of a solvent to form a solution; and then adding the entire solution to a vessel containing a second volume of a non-solvent, forming a solvent/non-solvent slurry, thereby causing fluticasone propionate to crystallise out of the solution as crystalline Form 1; wherein the solvent comprises acetone and from 0% to 10% water, based on the volume of the solvent; wherein the non-solvent comprises water and from 0% to 25% acetone, based on the volume of the non-solvent; wherein after the step of adding the entire solution to the non-solvent is completed, the solvent/non-solvent slurry is stirred in said vessel over a period of between about 1 and about 12 hours followed by filtration of the slurry to recover fluticasone propionate as crystalline Form 1 and drying of the recovered fluticasone propionate; and wherein the process is a batch process, and the controlled particle size has a 10th percentile volume diameter D[v, 0.1] of between 1.3 microns and 3.4 microns; a 50th percentile volume diameter D[v, 0.5] of between 2.8 microns and 11.4 microns; and a 90th percentile volume diameter D [v, 0.9] of between 5.6 microns and 32.1 microns.

15. The process according to claim 14, wherein the period of time is between about 1 and about 8 hours.

16. A process for preparing fluticasone propionate as crystalline polymorphic Form 1 having a defined median particle size, comprising: dissolving fluticasone propionate in a first volume of a solvent 'to form a solution; then adding the entire solution to a container of a second volume of a water-containing nonsolvent, thereby causing fluticasone propionate to crystallize out of the solution as crystalline Form 1 in a solvent/non-solvent slurry and, after the adding the entire solution is completed; stirring the solvent/non-solvent slurry in the container for a period of between about 1 and about 12 hours in the absence of ultrasound; and removing the solvent/non-solvent slurry from the container after the stirring and recovering fluticasone propionate Form 1 by filtration of the solvent/non-solvent slurry, wherein the solvent comprises acetone and from 0% to 10% water, based on the volume of the solvent; and wherein the non-solvent comprises water and from 0% to 25% acetone, based on the volume of the non-solvent; and, wherein the process is a batch process, and the controlled particle size has a 10th percentile volume diameter D[v, 0.1] of between 1.3 microns and 3.4 microns; a 50th percentile volume diameter D[v, 0.5] of between 2.8 microns and 11.4 microns; and a 90th percentile volume diameter D [v, 0.9] of between 5.6 microns and 32.1 microns.

17. The process according to claim 16, wherein the non-solvent is pure water, and the defined median particle size is between about 2.8 microns and about 6.7 microns.

18. The process according to claim 16, wherein the non-solvent comprises water and 25% acetone, and the defined median particle size is between about 11.4 microns and about 20 microns.

19. The process according to claim 16, wherein the period of time is between about 1 and about 8 hours.

\* \* \* \* \*